(12) United States Patent
Telfort et al.

(10) Patent No.: US 12,220,207 B2
(45) Date of Patent: Feb. 11, 2025

(54) NON-CONTACT CORE BODY TEMPERATURE MEASUREMENT SYSTEMS AND METHODS

(71) Applicant: Masimo Corporation, Irvine, CA (US)

(72) Inventors: Valery G. Telfort, Irvine, CA (US); Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 1099 days.

(21) Appl. No.: 16/802,351

(22) Filed: Feb. 26, 2020

(65) Prior Publication Data

US 2020/0275841 A1    Sep. 3, 2020

Related U.S. Application Data

(60) Provisional application No. 62/840,584, filed on Apr. 30, 2019, provisional application No. 62/810,718, filed on Feb. 26, 2019.

(51) Int. Cl.
*A61B 5/01* (2006.01)
*A61B 5/00* (2006.01)
*G01J 5/00* (2022.01)

(52) U.S. Cl.
CPC ............. *A61B 5/01* (2013.01); *A61B 5/0075* (2013.01); *A61B 5/7203* (2013.01); *A61B 5/7221* (2013.01); *A61B 5/742* (2013.01); *A61B 2560/0223* (2013.01); *G01J 5/00* (2013.01)

(58) Field of Classification Search
CPC ....... A61B 5/01; A61B 5/0075; A61B 5/7203; A61B 5/7221; A61B 5/742; A61B 2560/0223; A61B 2560/0252; G01J 5/00

USPC .......................................................... 374/120
See application file for complete search history.

(56) References Cited

U.S. PATENT DOCUMENTS

| | | | |
|---|---|---|---|
| 3,933,045 A | 1/1976 | Fox et al. | |
| 4,183,248 A | 1/1980 | West | |
| 4,245,500 A | 1/1981 | Malang | |
| 4,541,728 A | 9/1985 | Hauser et al. | |

(Continued)

FOREIGN PATENT DOCUMENTS

EP    0 979 394 B1    10/2001

OTHER PUBLICATIONS

US 2022/0192529 A1, 06/2022, Al-Ali et al. (withdrawn)

(Continued)

*Primary Examiner* — Catherine T. Rastovski
*Assistant Examiner* — Lal C Mang
(74) *Attorney, Agent, or Firm* — Knobbe, Martens, Olson & Bear, LLP

(57) ABSTRACT

A non-contact temperature measurement system for calculating estimated core body temperature is disclosed. The temperature measurement system can include a sensor that can detect the temperature of a patient and the temperature of ambient surrounding. The temperature of the patient and the ambient temperature can then be used to determine a core body temperature. The temperature measurement system includes an optical module having a light emitter and a light detector. The light emitter emits a beam of light towards the patient and the light detector detects a beam of light reflected by the patient. The reflected beam is analyzed to determine a distance between the temperature measurement system and the patient.

20 Claims, 12 Drawing Sheets

(56) References Cited

U.S. PATENT DOCUMENTS

| | | |
|---|---|---|
| 4,553,852 A | 11/1985 | Derderian et al. |
| 4,960,128 A | 10/1990 | Gordon et al. |
| 4,964,408 A | 10/1990 | Hink et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,816,706 A | 10/1998 | Heikkila et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,048,304 A | 4/2000 | Koch |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,196,714 B1 | 3/2001 | Bellifemine et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,280,397 B1 | 8/2001 | Yarden et al. |
| 6,285,896 B1 | 9/2001 | Tobler et al. |
| 6,292,685 B1 | 9/2001 | Pompei |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,527,439 B1 | 3/2003 | Bellofemine |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,886,978 B2 | 5/2005 | Tokita et al. |
| 6,920,345 B2 | 7/2005 | Al-Ali et al. |
| 6,929,611 B2 | 8/2005 | Koch |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,001,066 B1 | 2/2006 | Bellifemine |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,299,090 B2 | 11/2007 | Koch |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman et al. |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,153 B2 | 3/2009 | Blank et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |

(56) References Cited

U.S. PATENT DOCUMENTS

| | | |
|---|---|---|
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,789,554 B2 | 9/2010 | Sattler et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,981,046 B2 | 7/2011 | Yarden et al. |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 * | 4/2013 | Al-Ali ............... A61B 5/02416 600/323 |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,808,343 B2 * | 8/2014 | Koch ................ G16Z 99/00 600/549 |
| 8,821,010 B2 * | 9/2014 | Bellifemine ........ G01J 5/0022 600/549 |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,950,935 B1 | 2/2015 | Khachaturian et al. |
| 8,965,090 B1 | 2/2015 | Khachaturian et al. |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| D738,757 S | 9/2015 | Gross et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,262,826 B2 | 2/2016 | Khachaturian et al. |
| 9,267,572 B2 | 2/2016 | Barker et al. |
| 9,277,880 B2 | 3/2016 | Poeze et al. |
| 9,282,896 B2 | 3/2016 | Crawley et al. |
| 9,305,350 B2 | 4/2016 | Crawley et al. |
| 9,307,928 B1 | 4/2016 | Al-Ali et al. |
| 9,323,894 B2 | 4/2016 | Kiani |
| 9,324,144 B2 | 4/2016 | Khachaturian et al. |
| D755,392 S | 5/2016 | Hwang et al. |
| 9,326,712 B1 | 5/2016 | Kiani |
| 9,364,181 B2 | 6/2016 | Kiani et al. |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |

(56) References Cited

U.S. PATENT DOCUMENTS

| | | |
|---|---|---|
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,048,134 B2 * | 8/2018 | Yildizyan ............. G01J 5/0025 |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Ai-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,575,779 B2 | 3/2020 | Poeze et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |

(56) References Cited

U.S. PATENT DOCUMENTS

| | | |
|---|---|---|
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| 12,029,844 B2 | 7/2024 | Pauley et al. |
| 12,048,534 B2 | 7/2024 | Vo et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0038080 A1 | 3/2002 | Makarewicz et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0032893 A1 | 2/2003 | Koch |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2003/0225323 A1 | 12/2003 | Kiani et al. |
| 2004/0039271 A1 | 2/2004 | Blank et al. |
| 2004/0106163 A1 | 6/2004 | Workman, Jr. et al. |
| 2005/0024583 A1 | 2/2005 | Neuberger |
| 2005/0043631 A1 | 2/2005 | Fraden |
| 2005/0055276 A1 | 3/2005 | Kiani et al. |
| 2005/0101843 A1 | 5/2005 | Quinn et al. |
| 2005/0234317 A1 | 10/2005 | Kiani |
| 2005/0277819 A1 | 12/2005 | Kiani et al. |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0107736 A1 | 5/2007 | Karasek |
| 2007/0180140 A1 | 8/2007 | Welch et al. |
| 2007/0244377 A1 | 10/2007 | Cozad et al. |
| 2007/0282218 A1 | 12/2007 | Yarden |
| 2008/0064965 A1 | 3/2008 | Jay et al. |
| 2008/0077044 A1* | 3/2008 | Nakayama .............. A61B 5/01 600/549 |
| 2008/0094228 A1 | 4/2008 | Welch et al. |
| 2008/0103375 A1 | 5/2008 | Kiani |
| 2008/0200783 A9 | 8/2008 | Blank et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0296773 A1 | 12/2009 | Sattler |
| 2009/0299682 A1 | 12/2009 | Yarden |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0121217 A1 | 5/2010 | Padiy et al. |
| 2010/0234718 A1 | 9/2010 | Sampath et al. |
| 2010/0268113 A1 | 10/2010 | Bieberich |
| 2010/0270257 A1 | 10/2010 | Wachman et al. |
| 2010/0292605 A1 | 11/2010 | Grassl et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0051776 A1 | 3/2011 | Bieberich et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0144527 A1 | 6/2011 | He et al. |
| 2011/0158284 A1 | 6/2011 | Goto |
| 2011/0172498 A1 | 7/2011 | Olsen et al. |
| 2011/0230733 A1 | 9/2011 | Al-Ali |
| 2011/0249699 A1 | 10/2011 | Bieberich et al. |
| 2012/0065540 A1 | 3/2012 | Yarden et al. |
| 2012/0083710 A1 | 4/2012 | Yarden |
| 2012/0123231 A1 | 5/2012 | O'Reilly |
| 2012/0165629 A1 | 6/2012 | Merritt et al. |
| 2012/0172748 A1 | 7/2012 | Dunn |
| 2012/0209084 A1 | 8/2012 | Olsen et al. |
| 2012/0226117 A1 | 9/2012 | Lamego et al. |
| 2012/0238901 A1 | 9/2012 | Augustine |
| 2012/0283524 A1 | 11/2012 | Kiani et al. |
| 2013/0023775 A1 | 1/2013 | Lamego et al. |
| 2013/0030316 A1 | 1/2013 | Popov et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0331728 A1 | 12/2013 | Sun et al. |
| 2013/0345921 A1 | 12/2013 | Al-Ali et al. |
| 2014/0081100 A1* | 3/2014 | Muhsin ............... A61B 5/0002 600/324 |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275808 A1 | 9/2014 | Poeze et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106121 A1 | 4/2015 | Muhsin et al. |
| 2015/0282457 A1 | 10/2015 | Yarden |
| 2016/0196388 A1 | 7/2016 | Lamego |
| 2016/0367173 A1 | 12/2016 | Dalvi et al. |
| 2017/0000347 A1 | 1/2017 | Meftah et al. |

(56) References Cited

U.S. PATENT DOCUMENTS

| | | |
|---|---|---|
| 2017/0000391 A1* | 1/2017 | Wasson .................. G16H 50/20 |
| 2017/0024748 A1 | 1/2017 | Haider |
| 2017/0042488 A1 | 2/2017 | Muhsin |
| 2017/0055896 A1 | 3/2017 | Al-Ali |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0199871 A1 | 7/2018 | Pauley et al. |
| 2018/0213583 A1 | 7/2018 | Al-Ali |
| 2018/0242850 A1 | 8/2018 | Ellis et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0281286 A1* | 10/2018 | Vilajosana ............ B29C 64/393 |
| 2018/0289325 A1 | 10/2018 | Poeze et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0224434 A1 | 7/2019 | Silver et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060545 A1 | 2/2020 | Maher et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |

OTHER PUBLICATIONS

US 2024/0016391 A1, 01/2024, Lapotko et al. (withdrawn)

Tan, Li. Multirate DSP, part 1: Upsampling and downsampling EE Times Designline. https://www.eetimes.com/multirate-dsp-part-1-upsampling-and-downsampling/ (Year: 2008).*

"Multirate DSP, part 1: Upsampling and downsampling", Tan, Li; EE Times, Signal Processing | Designlines, Published Apr. 21, 2008; https://www.eetimes.com/multirate-dsp-part-1-upsampling-and-downsampling/ (Year: 2008).*

Haugk et al., "Temperature Monitored on the Cuff Surface of an Endotracheal Tube Reflects Body Temperature", Critical Care Medicine, 2010, vol. 38, No. 7, pp. 1569-1573.

Jay et al., "Skin Temperature Over the Carotid Artery Provides an Accurate Noninvasive Estimation of Core Temperature in Infants and Young Children During General Anesthesia", Pediatric Anesthesia, vol. 23, No. 12, Dec. 2013, pp. 1109-1116.

* cited by examiner

NON-CONTACT CORE BODY TEMPERATURE MEASUREMENT SYSTEMS AND METHODS

RELATED APPLICATIONS

Any and all applications for which a domestic priority claim is identified in the Application Data Sheet of the present application are hereby incorporated by reference under 37 CFR 1.57. This application is related to U.S. application Ser. No. 16/802,434, filed on Feb. 26, 2020, titled "Respiratory Core Body Temperature Measurement Systems and Methods" and U.S. application Ser. No. 16/546,667, filed on Aug. 1, 2019, titled "Core Body Temperature Measurement." Each of the above-referenced applications is hereby incorporated by reference in its entirety.

FIELD

The present disclosure relates to systems and methods of calculating estimated core body temperature.

BACKGROUND

Temperature is often a good indicator of patient health. Temperatures that are too low or high can negatively impact patient's metabolic rate, organ function, or cause tissue damage. Accurately measurement and monitoring of temperature of a patient, therefore, can be vital to care providers. Although one's temperature in peripheral regions (including, for example, hands, feet, legs, and arms) can vary (between 27° C. and 32° C.), the core temperature of deep tissues and internal organs remain relatively constant (between 36.5° C. and 37.2° C.). By measuring or observing changes in core temperature, harmful conditions such as infections, cardiac arrest, stroke, or other types of trauma can be observed.

SUMMARY

The present disclosure provides systems and methods of determining estimated core body temperature without direct physical contact with the patient. A sensor system can include a temperature sensor that determines skin temperature of a patient. In some examples, the sensor system also measures an ambient temperature. The sensor system can use the skin temperature or ambient temperature to calculate an estimated core body temperature. The sensor system can include a display module that can display the estimated core body temperature in different color schemes based on the estimated core body temperature reading. The sensor system can include one or more indicators that allow care providers to orient the sensor system at a correct distance away from the patient for more accurate measurements.

According to an aspect, a method for calibrating a sensor is disclosed. The method can include measuring, using a sensor, a first observed temperature of a first reference object having a first actual temperature, a second observed temperature of a second reference object having a second actual temperature, a third observed temperature of a third reference object having a third actual temperature, and a fourth observed temperature of a fourth reference object having a fourth actual temperature. The method can further include determining a difference between the first actual temperature and the first observed temperature as a first bias, a difference between the second actual temperature and the second observed temperature as a second bias, a difference between the third actual temperature and the third observed temperature as a third bias, and a difference between the fourth observed temperature and the fourth actual temperature as a fourth bias. The method can further include determining an offset for the sensor based at least on the first bias, the second bias, the third bias, and the fourth bias.

The first reference object can be a physical body at a thermal equilibrium. The second reference object can be a gallium triple point black body. The third reference object can be water in a water bath. The fourth reference object can be an infrared reference source with controlled temperature.

According to another aspect, a system for displaying a distance indicator associated with a distance between a temperature measurement system and a patient is disclosed. The system can include a first display module that can generate a first indicator. The first indicator can be projected at a first angle from a temperature measurement system towards a patient. The system can further include a second display module that can generate a second indicator. The second indicator can be projected at a second angle from the temperature measurement system towards the patient. The first indicator and the second indicator can intersect at a predetermined distance from the temperature measurement system such that the first indicator and the second indicator generate a third indicator projected on the patient when the temperature measurement system is positioned at the predetermined distance from the patient. The first indicator and the second indicator can be separately projected on the patient when the temperature measurement system is not positioned at the predetermined distance from the patient.

The first display module and the second display module can be positioned a first distance apart from each other. The first distance can be based at least on the first angle, the second angle, and the predetermined distance. The first indicator can be a first beam of light in a first color and the second indicator can be a second beam of light in a second color. The third indicator can be in a third color different from the first color and the second color. The first indicator and the second indicator can be associated with temperature of a patient.

According to another aspect, a system for displaying a distance indicator associated with a distance between a temperature measurement system and a patient is disclosed. The system can include one or more sensors that can collect a first plurality of data associated with temperature of a patient. The system can further include a processor that can calculate estimated core body temperature of the patient using the first plurality of data. The system can further include a first display module that can generate a first indicator that can be projected on the patient. The first indicator can display a first display when a temperature measurement system is at a first distance from a patient. The first indicator can display a second display when the temperature measurement system is at a second distance from the patient. The first indicator can be associated with the estimated core body temperature of the patient. The second distance can be different from the first distance. The first display can be illegible and the second display can be legible.

The first indicator can be in a first color. The first color can be based at least on the estimated core body temperature of the patient.

According to another aspect, a system for determining an estimated core body temperature is disclosed. The system can include a hardware processor programmed to execute software instructions. The hardware processor can cause the system to receive a first plurality of data from a first sensor.

The hardware processor can further cause the system to discard a first subset of the first plurality of data based at least on signal density distribution of the first plurality of data. The hardware processor can further cause the system to discard a second subset of the first plurality of data based at least on signal quality index of the first plurality of data. The hardware processor can further cause the system to receive a second plurality of data from a second sensor. The second plurality of data can be associated with ambient temperature. The hardware processor can further cause the system to calculate an estimated core body temperature based at least on a remainder of the first plurality of data and the second plurality of data.

The first plurality of data can be associated with skin temperature of a patient. The first subset of the first plurality of data can represent data within the first plurality of data that is not within a predetermined range of signal density of the first plurality of data. The second subset of the first plurality of data can represent data within the first plurality of data that has signal quality index lower than a predetermined value.

According to another aspect, a system for generating a display associated with temperature of a patient is disclosed. The system can include one or more sensors that can generate a plurality of data associated with temperature of a patient. The system can further include a processor operatively connected to the one or more sensors to receive the plurality of data from the one or more sensors. The processor can be programmed to execute software instructions to calculate an estimated core body temperature of the patient. The system can further include a display module operatively connected to the processor. The display module can generate and display an indicator associated with the estimated core body temperature. The indicator can include a first variable characteristic based at least on the estimated core body temperature.

The first variable characteristic can be a color of the indicator. The indicator can have a second variable characteristic based at least on the estimated core body temperature. The second variable characteristic can be a frequency at which the indicator is displayed. The indicator can blink at a predetermined frequency when the estimated core body temperature is above a threshold temperature.

According to another aspect, a temperature measurement system for determining an estimated core body temperature is disclosed. The temperature measurement system can include a first sensor that can collect a first plurality of data associated with temperature of a patient. The temperature measurement system can further include a light emitter for emitting a first beam of light towards the patient. The temperature measurement system can further include a light detector for detecting a second beam of light from the patient. The temperature measurement system can further include an aperture. The temperature measurement system can further include a cover for the aperture, the cover having an open configuration and a closed configuration, the cover in the open configuration allowing the first beam of light and the second beam of light to travel between the temperature measurement system and the patient, the cover in the closed configuration preventing the first beam of light and the second beam of light from travelling between the temperature measurement system and the patient. The temperature measurement system can further include a processor in electronic communication with the first sensor, the light emitter, and the light detector, the processor can calculate an estimated core body temperature of the patient based at least on the first plurality of data, the processor can determine a distance between the temperature measurement system and the patient based at least on the second beam of light. The temperature measurement system can further include a display module that can generate a first indicator projected on the patient, the first indicator having a first configuration when the temperature measurement system is at a predetermined distance from the patient and having a second configuration when the temperature measurement system is not at the predetermined distance from the patient.

The second beam of light can include at least a portion of the first beam of light reflected by the patient. The cover can provide a waterproof or water-resistant seal for the aperture. The cover can be a mechanical flap. The light detector can determine an intensity of the second beam of light. The light detector can determine an incident position of the second beam of light. The processor can determine the distance between the temperature measurement system and the patient based at least on the intensity or the incident position of the second beam of light.

The first sensor can be an infrared light sensor. The light emitter can be an infrared light sensor. The first indicator can represent an estimated core body temperature of the patient. The first indicator can be legible when in the first configuration and illegible when in the second configuration. The first indicator in the first configuration and the first indicator in the second configuration can differ in color. The light emitter and the light detector can be housed within the aperture. The aperture can have a substantially parabolic cross-section. The substantially parabolic cross-section of the aperture can aid in focusing the second beam of light towards the light detector.

According to another aspect, a method of generating a display indicative that a temperature measurement system is at a recommended distance from a patient is disclosed. The method can include actuating a cover to expose the aperture. The method can further include emitting, using a light emitter, a first beam of light towards the patient. The method can further include detecting, using a light detector, a second beam of light from the patient. The method can further include analyzing the second beam of light to determine a first distance between the temperature measurement system and the patient. The method can further include comparing the first distance to a predetermined range. The method can further include generating and displaying a first indicator upon determination that the first distance is not within the predetermined range. The method can further include generating and displaying a second indicator upon determination that the first distance is not within the predetermined range.

The analyzing the second beam of light can include determining an intensity of the second beam of light. The analyzing the second beam of light cam include determining an incident position of the second beam of light. The actuating the cover can include changing a configuration of the cover from a closed configuration to an open configuration. The cover in the open configuration can allow the first beam of light and the second beam of light to travel between the temperature measurement system and the patient, and the cover in the closed configuration can prevent the first beam of light and the second beam of light from travelling between the temperature measurement system and the patient.

The systems and methods for obtaining and monitoring estimated core body temperature disclosed herein have several features, no single one of which is solely responsible for their desirable attributes. Without limiting the scope as expressed by the claims that follow, certain features of the temperature system will now be discussed briefly. One skilled in the art will understand how the features of the disclosed technology provide several advantages over traditional systems and methods.

BRIEF DESCRIPTION OF THE DRAWINGS

Various examples will be described hereinafter with reference to the accompanying drawings. The drawings and the associated descriptions are provided to illustrate examples of the present disclosure and do not limit the scope of the claims. In the drawings, similar elements have similar reference numerals.

While the foregoing "Brief Description of the Drawings" references generally various examples of the disclosure, an artisan will recognize from the disclosure herein that such examples are not mutually exclusive. Rather, the artisan would recognize a myriad of combinations of some or all of such examples.

DETAILED DESCRIPTION

Temperature Measurement System

Although certain examples of temperature measurement system are described herein, this disclosure extends beyond the specifically disclosed examples and/or uses and obvious modifications and equivalents thereof. Thus, it is intended that the scope of this disclosure should not be limited by any particular examples described below.

Figure 1A:
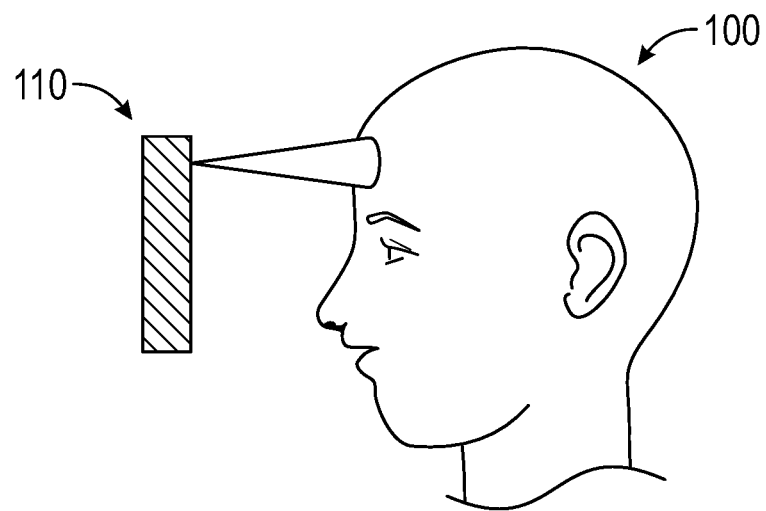
FIG. 1A illustrates an embodiment of a sensor system collecting data associated with temperature of a patient.

FIG. 1A illustrates an example of a non-contact temperature measurement system 110 for measuring temperature of a patient 100 by taking a temperature measurement at the patient's forehead. The temperature measurement system 110 may include one or more sensors that can collect data associated with temperature of a patient. In some examples, the one or more sensors of the temperature measurement system 110 may be an infrared temperature sensor that can collect data associated with temperature of a patient without being in contact with the patient. Taking temperature measurement at the patient's forehead can be advantageous because it allows care providers to measure patient temperature without having to reorient or move patients. In some examples, the temperature measurement system 110 may provide more accurate reading when positioned at a recommended distance from the patient 100. The temperature measurement system may be Rad-G™ Pulse Oximeter available at Masimo Corporation, Irvine, CA.

In some examples, the temperature measurement system 110 may be in contact with a patient when determining temperature of a patient. Various examples of contact-based temperature measurement systems are disclosed in U.S. application Ser. No. 16/802,434, filed on Feb. 26, 2020, titled "Respiratory Core Body Temperature Measurement Systems and Methods," entirety of which is incorporated by reference in its entirety herein.

Figure 1B:
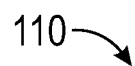
FIG. 1B illustrates an example schematic diagram of the sensor system of FIG. 1B.

FIG. 1B illustrates a block diagram of the temperature measurement system 110 shown in FIG. 1A. The temperature measurement system 110 can include a processor 120, a sensor 130, a display module 140, and a communication module 150. The processor 120 can be operatively connected to the sensor 130, the display module 140, and the communication module 150 such that it can receive signals from or transmit signals to the sensor 130, the display module 140, and the communication module 150.

The display module 140 can receive signals from the processor 120 and generate displays associated with temperature of a patient. The displays generated by the display module 140 may be based at least in part on the signals transmitted by/from the processor 120. For example, the display module 140 can generate and display numerical temperature readings of the patient. Optionally, the display module 140 can generate displays with different characteristics including, but not limited to, color, blinking frequency, and the like. For example, when patient temperature is above a recommended value or a predetermined threshold, the display module 140 may display temperature readings in red. In this regard, care providers and others can advantageously identify temperature readings greater than a recommended value or a predetermined threshold. Likewise, the display module 140 may display temperature readings in green when patient temperature is at or below the recommended value or the predetermined threshold. In other examples, the display module 140 can use different types or patterns of blinking to display temperature readings above the recommended value or the predetermined threshold.

The display module 140 can further display information associated with the orientation of the temperature measurement system 110. The orientation of the temperature measurement system 110 may be determined with respect to the patient 100. The display module 140 can generate displays that indicate whether the temperature measurement system 110 is at a recommended distance from the patient 100. This can be advantageous since some sensors require the sensor to be at a certain, recommended distance from a heat source to accurately measure temperature of the heat source. Further information regarding the display module 140 and the displays generated by the display module 140 is described herein.

In some examples, the display module 140 may generate displays that may be legible when the distance between the temperature measurement system 110 and the patient satisfies a condition. The condition may be associated with a predetermined distance value (for example, 10 inches). The condition may be changed by users, for example, care providers.

The communication module 150 can allow the temperature measurement system 110 to communicate with other sensor systems 110 or devices. For example, the temperature measurement system 110 can communicate with nearby pulse oximeter sensors via the communication module 150 to receive data related to patient blood perfusion. This can be advantageous since blood perfusion can be related to core body temperature of the patient and therefore affect calculation of the estimated core body temperature. The communication module 150 may be capable of establishing one or more types of wireless communications including, but not limited to, near-field communication, Wi-Fi, Li-Fi, LTE, 3G, 4G, and the like. In some examples, the temperature measurement system 110 may wirelessly store data in a remote server via wireless communication established by the communication module 150.

Types of Sensors

The sensor(s) 130, as described herein, may be able to generate data associated with the temperature of a patient. The sensor 130 may be an infrared (IR) sensor capable of detecting or measuring infrared radiation from an object. In a non-limiting example, the sensor 130 can detect infrared radiation and convert that infrared radiation into an electronic signal (including, for example, current or voltage) that correspond to the amount of infrared radiation. The sensor 130 can be an active or passive infrared sensor.

In some examples, the sensor 130 may be an infrared thermometer for non-contact temperatures measurements (for example, MLX090614 manufactured by Melexis Technologies NV, Tessenderlo, Belgium). In some examples, the sensor 130 may include a thermal relay that can allow an easy and cost effective implementation in temperature alert applications. A temperature threshold associated with temperature alerts may be programmable by a user, for example, a care provider. In some examples, the sensor 130 may include an optical filter to filter the visible or near infrared radiant flux. Such optional filter may be integrated into the sensor 130.

Temperature Measurements

As discussed above, the sensor 130 may measure infrared radiation from an object. In the example shown in FIG. 1A, the sensor 130 of the temperature measurement system 110 can measure infrared radiation from a patient's forehead. In other examples, the sensor 130 of the temperature measurement system 110 can measure infrared radiation from other parts of patient's body including, but not limited to, armpit, groin, and the like.

In some examples, the sensor 130 may measure ambient temperature in addition to measuring infrared radiation from a patient. The ambient temperature and the temperature of the patient can be used to calculate estimated core body temperature of the patient. Calculation of the estimated core body temperature using the ambient temperature and the patient temperature is further described herein.

Calculating Estimated Core Body Temperature

As discussed above, core body temperature serves as an important indicator of one's health. However, core body temperature can be difficult to measure or estimate. Although there are many methods to measure temperature that are proxy to core body temperature, their accuracy, latency, and invasiveness can vary greatly. For example, while measuring temperature in the pulmonary artery can often provide the great accuracy in estimating core body temperature, it is one of the most invasive methods. In another example, while measuring temperature at the eardrum provides low latency, low invasiveness, and great comfort for patients, it suffers from low accuracy. Therefore, it may be advantageous to provide a non-invasive method that can accurately estimate core body temperature.

In some examples, ambient temperature measurements and skin temperature measurements may be used to estimate core body temperature. Skin temperature measurements may be taken at a forehead of a patient as shown in FIG. 1A. In other examples, reference temperature measurements and skin temperature measurements may be used to estimate core body temperature.

Figure 2A:
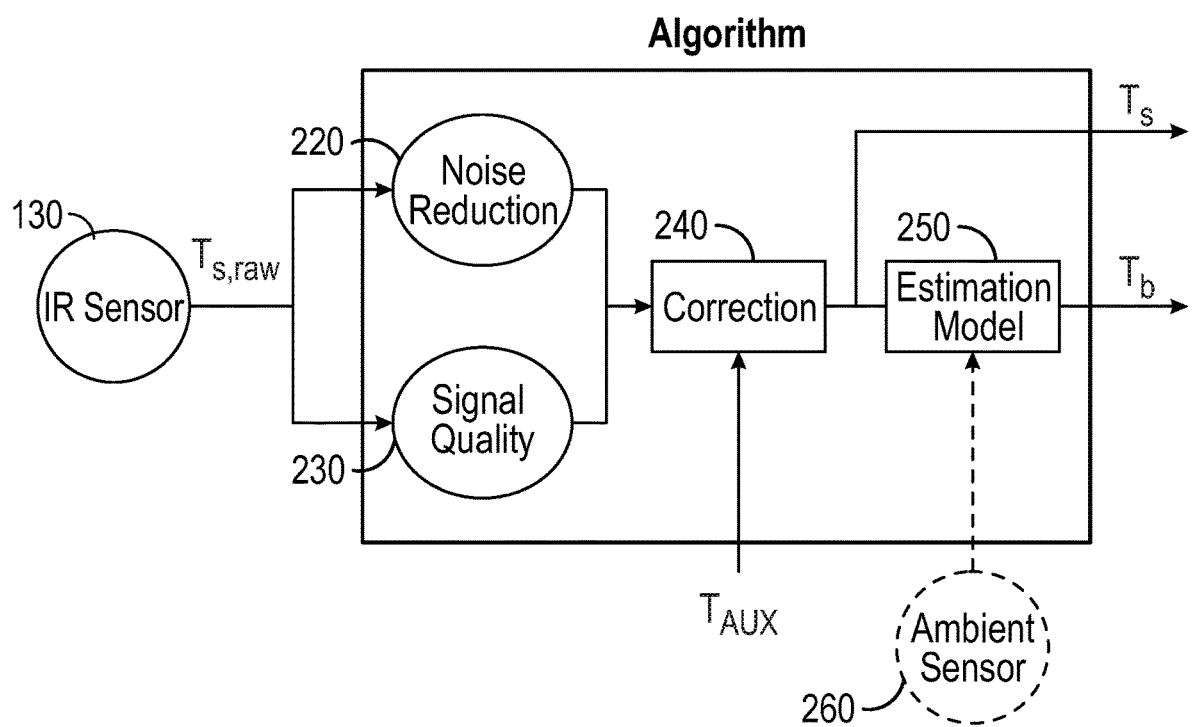
FIG. 2A illustrates a block diagram for an example method of calculating an estimated core body temperature.
Figure 2B:
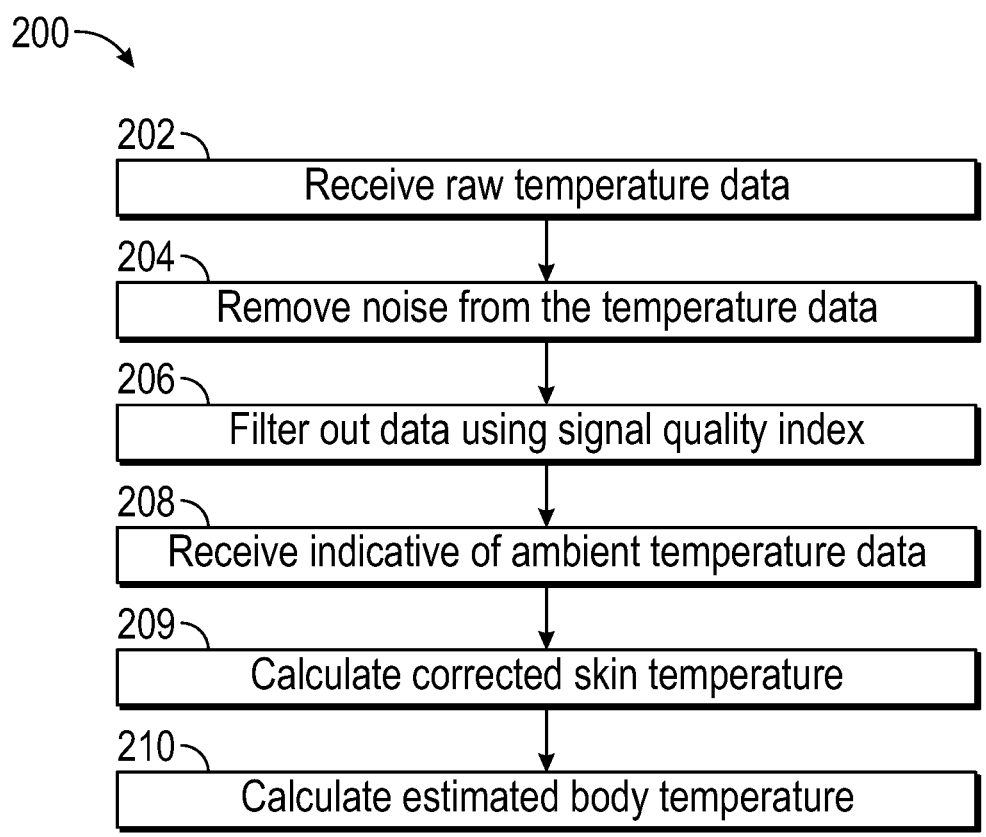
FIG. 2B illustrates another example method of calculating an estimated core body temperature.

Referring to FIGS. 2A and 2B, an example method of calculating estimated core body temperature is disclosed. As described herein, the sensor 130 may collect temperature data associated with a patient. For example, the temperature data may be raw temperature data (for example, $T_s$) associated with surface temperature of the skin of a patient. In some examples, the temperature data is collected from the forehead of a patient. Once the sensor 130 collects the temperature data, the temperature data can be transmitted to the processor 120 of the temperature measurement system 110.

As shown in FIG. 2A, the processor 120 may apply one or more processing methods including, for example, noise reduction and signal quality filtering. Such signal processing methods can advantageously improve the quality of the temperature data and allow for more accurate calculation of estimated core body temperature. At block 220, the processor 120 may reduce noise in the temperature data by removing data points that do not satisfy a predetermined condition. The predetermined condition may be provided by a care provider or by a manufacturer of the temperature measurement system. In some examples, the predetermined condition may be a tolerance associated with the sensor 130. In some examples, the tolerance may be specific to different sensors. In some examples, the tolerance may be an index associated with a standard deviation of a data collected by the sensor 130.

At block 230, the processor 120 can calculate signal quality index for filtering the temperature data collected by the sensor 130. The signal quality index may be compared to a predetermined condition to determine whether to remove or keep respective, corresponding data points. If the predetermined condition is not satisfied, the data point may not be used to estimate core body temperature. On the other hand, if the predetermined condition is satisfied, the data point may be used to estimate the core body temperature. In some examples, the predetermine condition may be satisfied if the signal quality index is above a threshold.

At block 240, the processor 120 can determine corrected (or adjusted) surface temperature (for example, skin temperature at the forehead of a patient) based at least in part on the processed temperature data. Optionally, the correction may also be based at least in part on temperature data indicative of ambient temperature (for example, $T_{aux}$ in FIG. 2A). The temperature data indicative of ambient temperature ($T_{aux}$) may be the actual ambient temperature or a proxy representative of the ambient temperature. The temperature indicative of ambient temperature may be collected by the sensor 130 or another temperature sensor.

At block 250, the processor 120 can calculate estimated core body temperature (for example, $T_b$ in FIG. 2A) based at least in part on the corrected surface temperature. Optionally, the estimated core body temperature may be determined based at least in part on the corrected surface temperature and the temperature indicative of ambient temperature, for example, collected by the sensor 130. Alternatively and/or optionally, the processor 120 may receive actual ambient temperature data from an ambient sensor 260 the estimated core body temperature may be determined based at least in part on the actual ambient temperature data.

FIG. 2B illustrates an example method 200 of calculating estimated core body temperature. At block 202, the temperature measurement system 110 can receive raw temperature data from the sensor 130. The raw temperature data may be indicative of surface temperature of skin of a patient. The raw temperature data can be temperature measurements collected at the forehead of the patient, as shown in FIG. 1A. The sensor 130, for example, can be an IR sensor.

The patient temperature data, for example, $T_s$ as shown in FIG. 2A, can be collected at a predetermined frequency that can be between about 1 Hz and about 10 kHz, between about 5 Hz and about 5 kHz, between about 10 Hz and about 1 kHz, between about 100 Hz and about 500 Hz, between about 200 Hz and about 400 Hz, or about 1 Hz, 5 Hz, 10 Hz, 50 Hz, 100 Hz, 250 Hz, 500 Hz, 1 kHz, 2 kHz, 5 kHz, 10 kHz, or range between any two of aforementioned values, and the like. The patient temperature data can be a raw data (including, for example, voltage or current) or processed data.

The processor 120 of the temperature measurement system 110 may process the raw temperature data (for example, $T_s$ in FIG. 2A) prior to calculating or determining estimated core body temperature (for example, $T_b$ in FIG. 2A). At block 204, inaccurate measurements or measurements not within a specified tolerance may be discarded using noise reduction process, as generally described herein in reference to block 220 of FIG. 2A. The processor 120 may compare sensor measurements (for example, temperature data) to a predetermined threshold condition to determine whether measurements may be inaccurate or not within a specified tolerance. In some examples, such predetermined threshold condition or such specific tolerance may be provided during manufacture of the sensors, for example, the sensor(s) 130. At block 206, measurements with signal quality index below a predetermined threshold value may be discarded, as generally described herein in reference to block 230 of FIG. 2A. Additional details of noise reduction process and monitoring of signal quality is described herein.

At block 208, the temperature measurement system 110 can receive temperature data indicative of ambient temperature of the area surrounding the patient. The temperature data indicative of the ambient temperature may be the actual ambient temperature or a proxy representative of the ambient temperature. The proxy representative of the ambient temperature may be, for example, a thermal gradient within the sensor 130 that can be used to adjust or compensate temperature measurements (for example, $T_s$). Optionally, one or more sensors different from the sensor 130, for example, separate from the temperature measurement system 110, may measure and provide temperature data indicative of the ambient temperature. In some examples, the ambient temperature may be measured or estimated by the sensor 130.

At block 209, the temperature measurement system 110 (or the processor 120 of the temperature measurement system 110) may calculate corrected skin temperature, as generally described herein in reference to block 240 of FIG. 2A. The corrected skin temperature may be calculated based at least in part on the temperature data indicative of ambient temperature and filtered or processed raw temperature data. At block 210, the temperature measurement system 110 can calculate the estimated core body temperature of the patient, as generally described herein in reference to block 250 of FIG. 2A. The estimated core body temperature may be calculated based at least in part on the corrected skin temperature and the temperature data indicative of ambient temperature. Optionally, in some examples, the estimation of core body temperature can be done based at least in part on the ambient temperature. The ambient temperature may be determined by the sensor 130, another sensor, or a device other than the temperature measurement system 110.

In some examples, multiple temperature measurements may be used to estimate core body temperature. In some examples, the multiple temperature measurements may be taken at one or more different parts or locations of a patient's body. Various examples of systems and methods of estimating core body temperature using multiple temperature measurements is disclosed in U.S. application Ser. No. 16/546,667, filed on Aug. 1, 2019, titled "Core Body Temperature Measurement," entirety of which is incorporated by reference herein.

Noise Reduction

Although an IR sensor may provide a non-invasive method to measure temperature, its measurements can include noise that may not accurately represent patient temperature. Therefore, it may be advantageous to identify and remove noise from temperature data (including, for example, ambient temperature measurements and skin temperature measurements) using notice reduction methods.

Figure 3A:
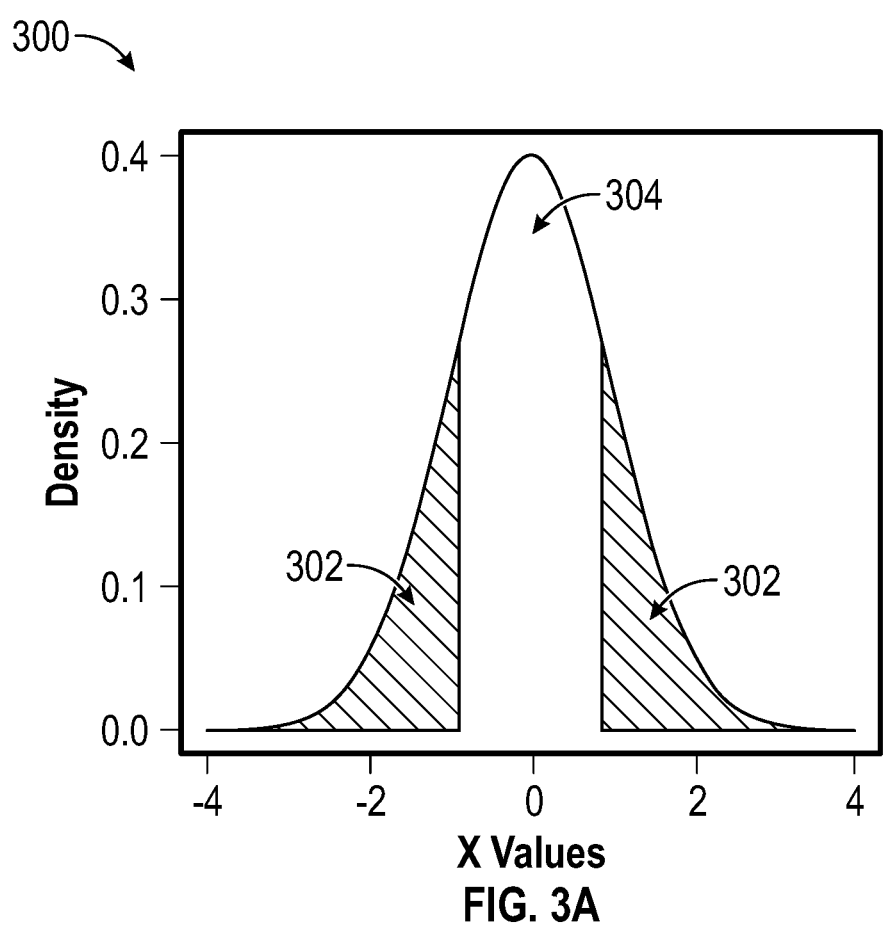
FIG. 3A is a graphical illustration of an example method of data noise reduction.

FIG. 3A shows an exemplary signal distribution graph 300, which illustrates distribution of the patient temperature data. In the example signal distribution graph 300, the y-axis represents signal density while the x-axis represents a delta between each data point of the patient temperature data and a mean value of the patient temperature data. The highlighted portion of the graph 300 may illustrate a subset 302 of the patient temperature data that may be determined or categorized as noise. The non-highlighted portion of the graph 300 may illustrate a subset 304 of the patient temperature data that may not be determined or categorized as noise. In some examples, the subset 304 of the temperature data may be used to estimate core body temperature. In some examples, the subset 302 may be determined using the distribution of the temperature data. In some examples, the subset 302 can be determined using other methods such as data smoothing, moving average filtering, Savitzky-Golay filtering, local regression filtering, robust local regression, and the like.

Figure 3B:
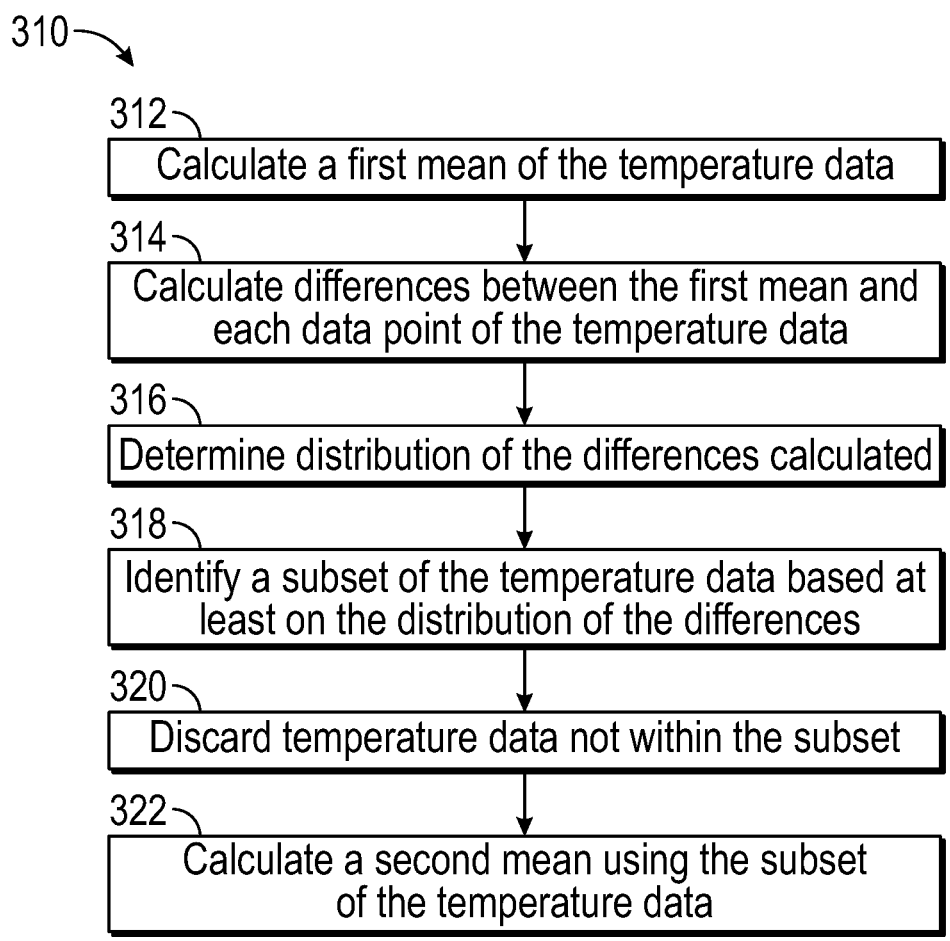
FIG. 3B illustrates another example method of data noise reduction.

FIG. 3B illustrates an example method 310 of reducing noise in the patient temperature data. At block 312, a mean of the patient temperature data is calculated. At block 314, differences between the mean and each data point of the patient temperature data are calculated. The differences between the first mean and each data point of the patient temperature data may be positive or negative. At block 316, a distribution of the difference (between the first mean and each data point of the patient temperature data) is determined.

At block 318, a subset of the patient temperature data may be identified, for example, the subset 304. In some examples, standard deviation from the mean may be used to identify data points to be included in the subset. For example, the subset may include data points that are within plus/minus one standard deviation from the mean, two standard deviations from the mean, three standard deviations from the mean, and the like. Once the subset is identified, data points that are not within the subset may be discarded at block 320. At block 322, another mean may be calculated using the subset identified at block 318. The mean calculated at block 322 may be used to determine a patient temperature reading.

Signal Quality Index

In some examples, the patient temperature data can be filtered using signal quality index (SQI). Using SQI to filter temperature data can be advantageous by discarding relatively inaccurate data and thereby achieving more accurate temperature reading of a patient.

Figure 4:
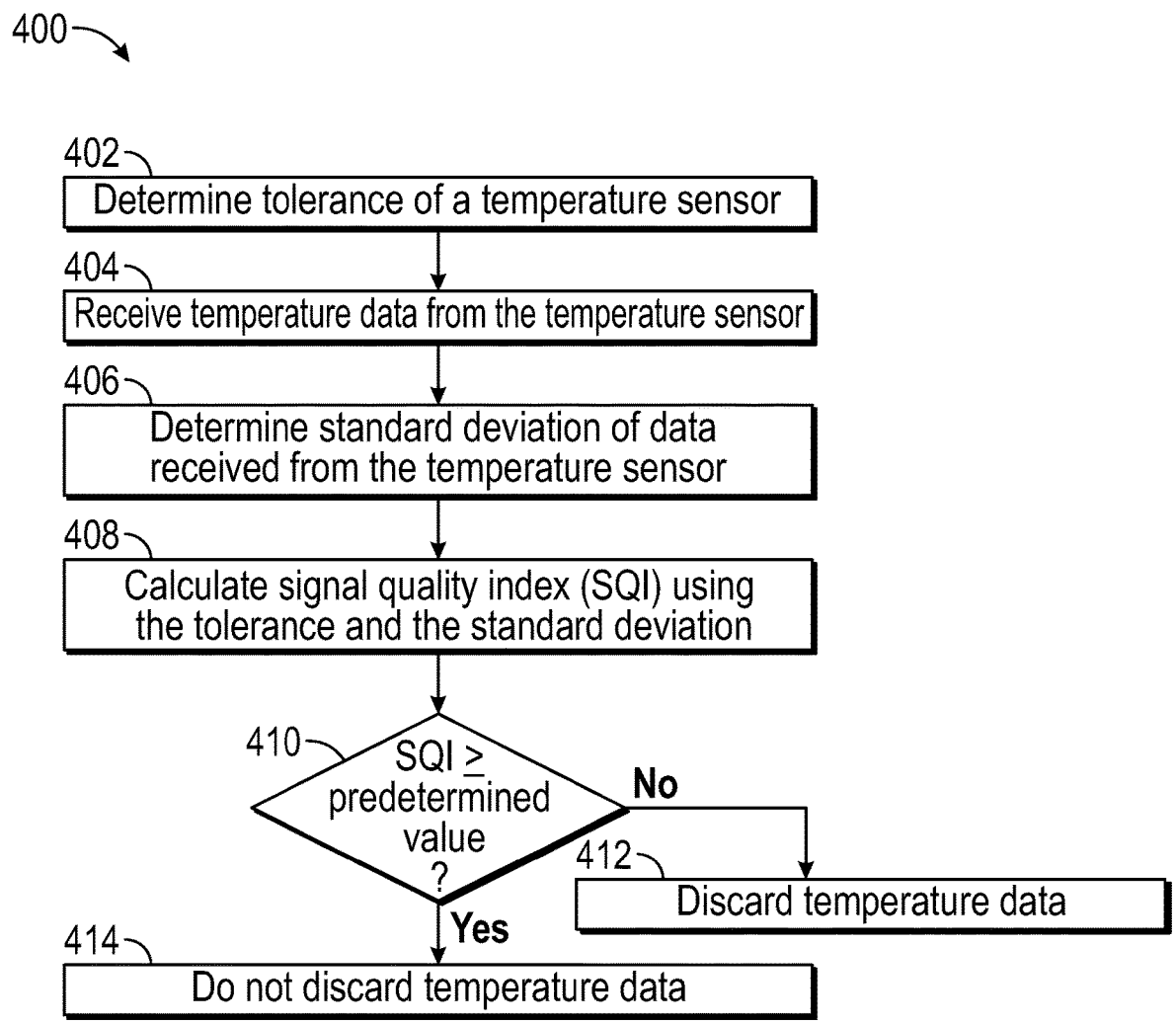
FIG. 4 illustrates an example method of filtering data using signal quality index.

FIG. 4 illustrates an example method 400 to filter data using SQI. At block 402, sensor tolerance is determined. Sensors can have tolerances that define total allowable error for sensor measurements. At block 404, standard deviation of the patient temperature data is calculated. At block 406, signal quality index is calculated for the patient temperature data. In some examples, the signal quality index (SQI) may be calculated using at least the sensor tolerance and the standard deviation of the patient temperature data. An exemplary equation for calculating the SQI is shown below.

$$SQI = \frac{100}{std(\text{signal})/\text{tolerance}}$$

In the equation shown above, SQI increases as standard deviation of the data becomes less than the tolerance of the sensor 130. On the other hand, SQI decreases as standard deviation of the data becomes greater than the tolerance of the sensor 130. At block 408, SQI of the patient temperature data may be compared to a predetermined threshold value. For example, the predetermined value can be 100. In some examples, care providers can provide or change the predetermined threshold value for SQI. If SQI is greater or equal to the predetermined threshold value, the patient temperature data may not be discarded at block 414. If SQI is less than the predetermined threshold value, the patient temperature data can be discarded at block 412. In some examples, the predetermined threshold value for SQI may vary over time or depend on patients or types of sensors used for temperature data measurement.

Physical Model

Figure 5A:
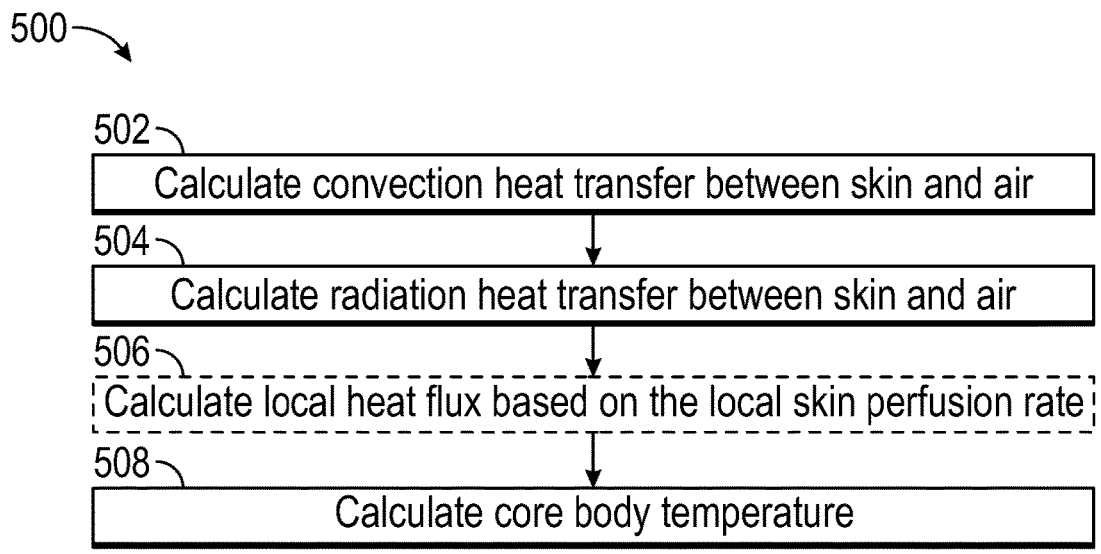
FIG. 5A illustrates an example method of calculating an estimated core body temperature.
Figure 5B:
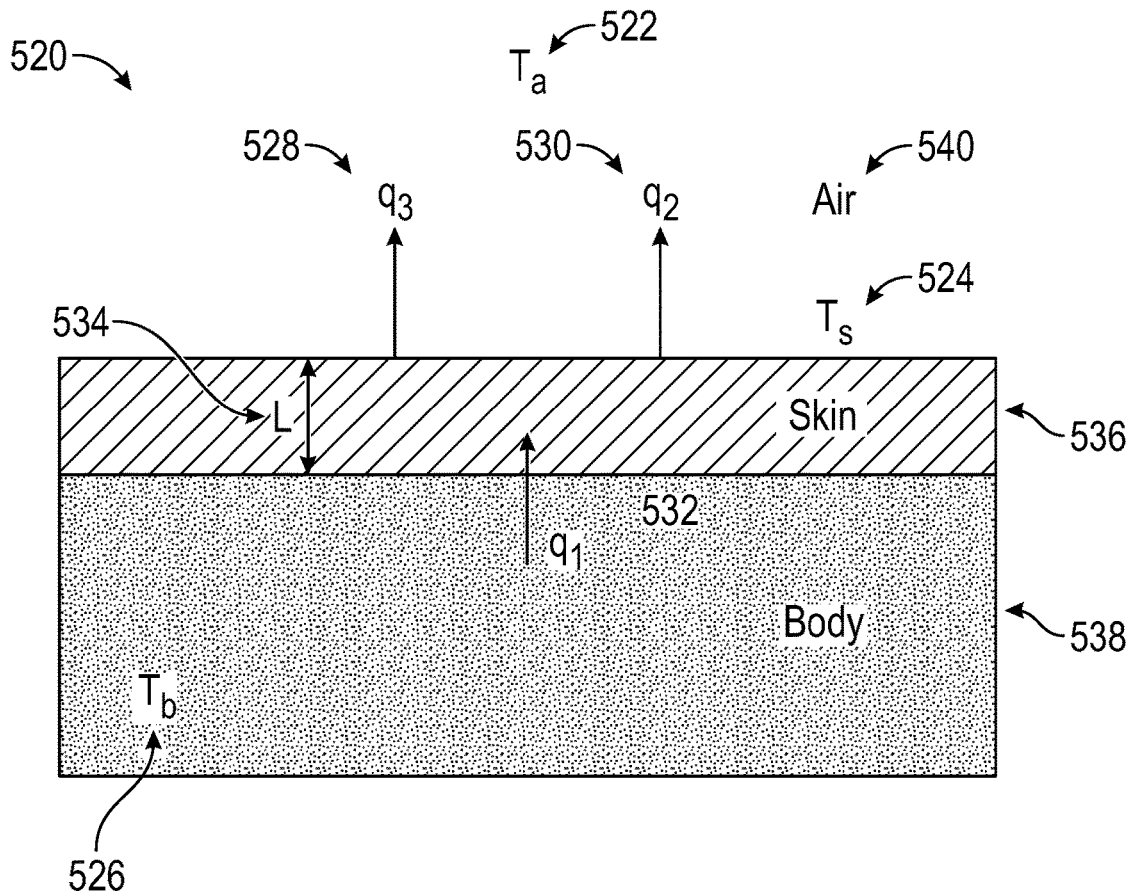
FIG. 5B illustrates a theoretical model for the method of calculating an estimated core body temperature of FIG. 5A.

Referring to FIGS. 5A-5B, a core body temperature may be estimated using a physical model. An example of a physical model may use an ambient temperature ($T_a$) and a skin temperature ($T_s$) of a patient to estimate core body temperature ($T_b$) the patient. The skin temperature may be measured at a forehead of a patient as shown in FIG. 1A. An exemplary method 500 of estimating core body temperature is shown in FIG. 5A.

At block 502, $T_s$ and $T_a$ are used to calculate convection heat transfer between the patient (for example, forehead of the patient) and the ambient surrounding. At block 504, $T_s$ and $T_a$ are used to calculate radiation heat transfer. At block 508, a core body temperature can be estimated using the convection heat transfer and the radiation heat transfer.

Optionally, a local heat flux may be estimated or calculated using a local skin perfusion rate at block 506. Local skin perfusion rate (for example, at a forehead of a patient) can change the amount of heat transfer between the skin and the air. For example, an increase in core body temperature can increase skin perfusion rate, thereby increasing heat transfer between the body and the skin and between the skin and the air.

FIG. 5B illustrates an example physical model 520 that may be used to estimate core body temperature 526 ($T_b$) of body 538 using ambient temperature 522 ($T_a$) of air 540 and skin temperature (or surface temperature) 524 ($T_s$) of skin 536 of a patient. In the physical model 520, three different types of thermal heat flux may be identified: conductive heat transfer 532 ($q_1$) between the body 538 and the skin 536, convective heat transfer ($q_2$) between the skin 536 and the air 540, and radiative heat transfer ($q_3$) between the skin 536 and the air 540. In some examples, the conductive heat transfer, the convective heat transfer, and the radiative heat transfer may be calculated using the following equations:

$$q_1 = k_\gamma * \frac{(T_b - T_s)}{L}$$

$$q_2 = h_{ra} * (T_s - T_a)$$

$$q_3 = \varepsilon_\gamma * \sigma * (T_s^5 - T_a^4)$$

where $k_\gamma$ represents thermal conductivity of human skin, L represents thickness 534 of the skin 536, $h_{ra}$ represents convective heat transfer coefficient of an ambient air, $\epsilon_\gamma$ represents emissivity coefficient of human skin, and $\sigma$ represents the Stefan-Boltzmann Constant (i.e., 5.6703*10$^{-8}$ (W/m$^2$K$^4$). Under a thermal equilibrium between the body, the skin, and the ambient surrounding, any heat transfer between the body and the skin can be equal to heat transfer between the skin and the ambient air. In other words, under thermal equilibrium, $q_1$ can be equal to a sum of $q_2$ and $q_3$. Using the above equations and known coefficients, core body temperature ($T_b$) may be calculated using equations shown below.

$$q_1 = q_2 + q_3$$

$$k_r * \frac{(T_b - T_s)}{L} = [h_{ra} * (T_s - T_a)] + [\varepsilon_r * \sigma * (T_s^4 - T_a^4)]$$

$$T_b = T_s + \frac{L}{k_r}[[h_{ra} * (T_s - T_a)] + [\varepsilon_r * \sigma * (T_s^4 - T_a^4)]]$$

Regression Model

Figure 5C:
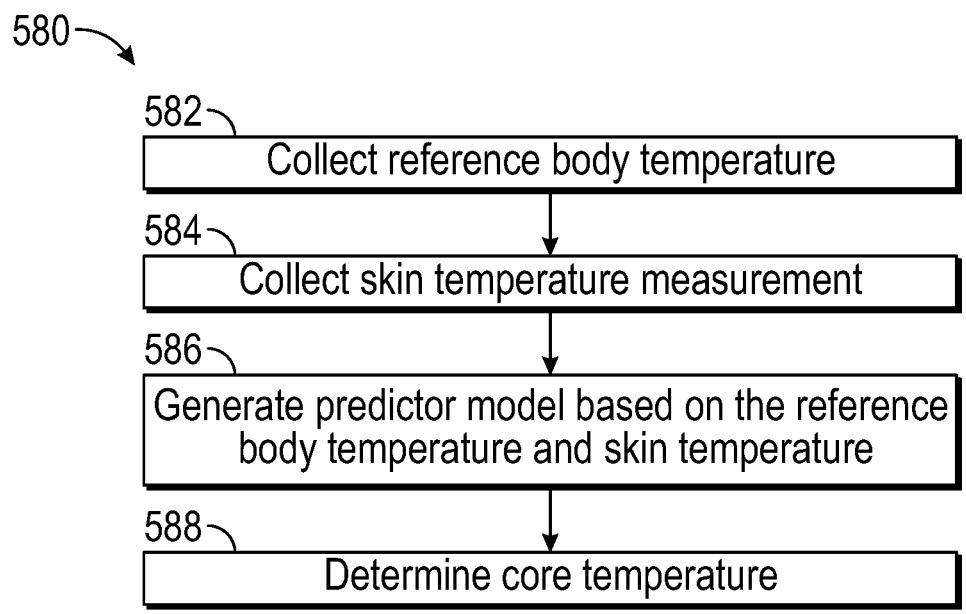
FIG. 5C illustrates another example method of calculating an estimated core body temperature.

Different methods may be used to estimate core body temperature of a patient. In a non-limiting example, linear regression may be used to estimate core body temperature of a patient. FIG. 5C illustrates an example method 580 to estimate core body temperature using a regression model between reference body temperature measurements and skin temperature measurements. At block 582, reference body temperature measurement can be collected. The reference temperature measurements may be collected at different locations of a patient's body such as eardrum and mouth. The reference temperatures can be proxy to core body temperature. At block 584, skin temperature measurements can be collected. At block 586, a mathematical model describing the relationship between the reference temperature measurements and the skin temperature measurements may be generated. In a non-limiting example, following exemplary regression model may be used between the reference temperature ($T_b$) and the skin temperature ($T_s$).

$$T_b = a_N * T_s^N + a_{N-1} * T_s^{N-1} + \ldots + a_2 * T_s^2 + a_1 * T_s + btas$$

Once the coefficients (for example, $a_n$, $a_{n-1}$, $a_{n-2}$, ... $a_2$, $a_1$) and the bias is determined, skin temperature may be used to estimate body temperature at block 588. In some examples, the coefficients and the bias may be specific to a patient. In other words, the coefficients and the bias may vary between different patients. In this regard, reference temperatures may be needed to determine the coefficients and the bias for an estimation model.

Display

Once estimated core body temperature is determined, it may be advantageous to display the estimated core body temperature to allow care providers and others to easily identify a temperature reading that is not within the normal range (for example, between 36.1° C. and 37.2° C. or 97° F. and 99° F.). In some examples, the estimated core body temperature may be displayed on a screen on the temperature measurement system 110 or projected on the patient 100 while collecting the temperature measurements. For example, the estimated core body temperature may be displayed or projected on a patient's forehead while the temperature measurement system 110 measures temperature at the patient's forehead. This configuration can be advantageous because it allows care providers to measure and record patient temperature without having to take their eyes off of the patient.

Figure 6:
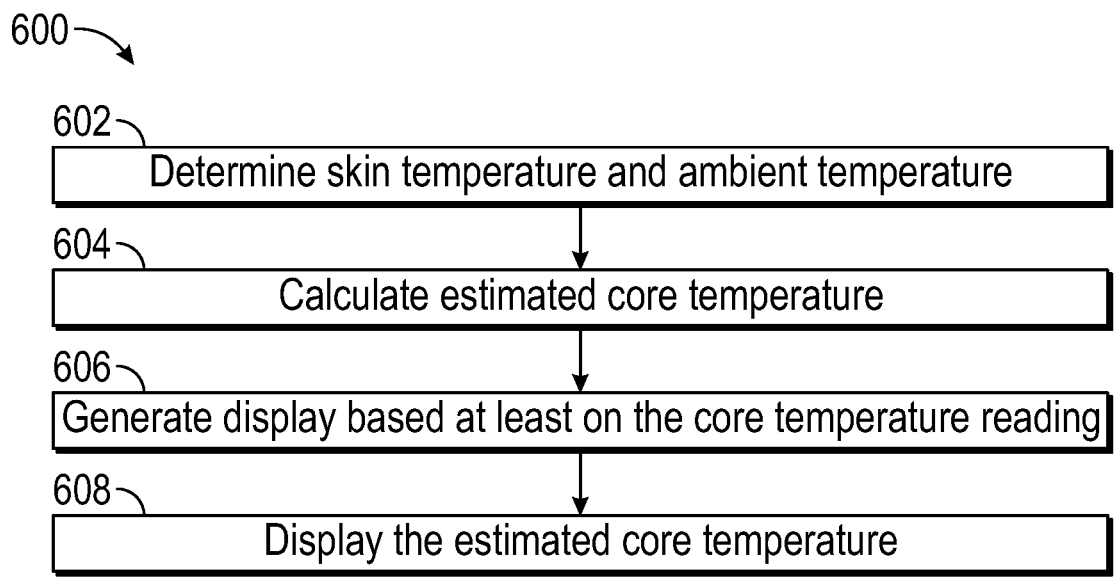
FIG. 6 illustrates an example method of displaying an estimated core body temperature.

FIG. 6 illustrates an example method 600 of displaying core temperature. At block 602, ambient temperature measurements and patient temperatures measurements can be collected as described herein. At block 604, estimated core body temperature can be calculated using methods or systems described herein. At block 606, temperature display can be generated based at least on the calculated estimated core body temperature. At block 608, the estimated core body temperature is displayed. In some examples, the estimated core body temperature may be displayed on a screen of the temperature measurement system 110. In some examples, the estimated core body temperature may be displayed or projected on a surface. For example, the estimated core body temperature may be displayed on a skin of a patient. In some examples, the estimated core body temperature may be displayed on a forehead of a patient. In some examples, the estimated core body temperature may be displayed on an area of a patient's skin corresponding to where the sensor 130 took measurements associated with the temperature of the patient.

In some examples, one or more characteristics of the display, for example, generated by the display module 140, may vary depending on the estimated core body temperature. When the estimated core body temperature is above the normal range (for example, hyperthermia), the display of the estimated core body temperature may be in red. On the other hand, when the estimated core body temperature is below the normal range (for example, hypothermia), the display of the estimated core body temperature may be in blue. When the estimated core body temperature is within the normal range, the display of the estimated core body temperature may be in green. In some examples, different visible blinking or flashing patterns may be used for different estimated core body temperatures. The display of the estimated core body temperature may be steady and not blink when the estimated core body temperature is within the normal range. However, the display may blink when the estimated core body temperature is not within the normal range. In other examples, the display may blink at a variable rate depending on the difference between the measured estimated core body temperature and the normal range. Of course, other suitable colors and patterns not described above may be used to display the estimated core body temperature.

The frequency at which the display of the estimated core body temperature blink or flash may be between about 1 Hz and about 50 Hz, between about 2 Hz, and about 45 Hz, between about 5 Hz, and about 40 Hz, between about 10 Hz, and about 35 Hz, between about 15 Hz and about 30 Hz, between about 20 Hz and about 25 Hz, or about 1 Hz, 2 Hz, 5 Hz, 10 Hz, 15 Hz, 20 Hz, 25 Hz, 30 Hz, 35 Hz, 40 Hz, 45 Hz, 50 Hz, or range between any two of aforementioned values.

In some examples, the color schemes (or blinking or flashing patterns) may be provided by the processor 120 of the temperature measurement system 110. In other examples, such schemes or patterns may be provided by care providers. For example, care providers may be able to configure the temperature measurement system 110 or the display module 140 to change the color schemes or blinking (or flashing) patterns. Care providers may be able to remotely configure the temperature measurement system 110 or the display module 140 via the communication module 150. For example, care providers may transmit signals that include color (or blinking) schemes or patterns to the temperature measurement system 110 via the communication module 150 using mobile devices including, but not limited to, tablets, mobile communication devices, personal computers, and the like.

Distance Indicators

As described herein, the sensor 130 can be an IR sensor. Typically, IR sensors have a recommended measuring range. For example, when the sensor 130 is too close or too far from a patient, the temperature measurement system 110 may not be able to accurately estimate core body temperature of the patient. Therefore it may be advantageous to provide systems or methods for indicating when the sensor 130 is located at an adequate or recommended distance from the patient. The recommended distance for the sensor 130 may be determined at the time of manufacture or changed by a user, for example, a care provider, at any time.

Figure 7:
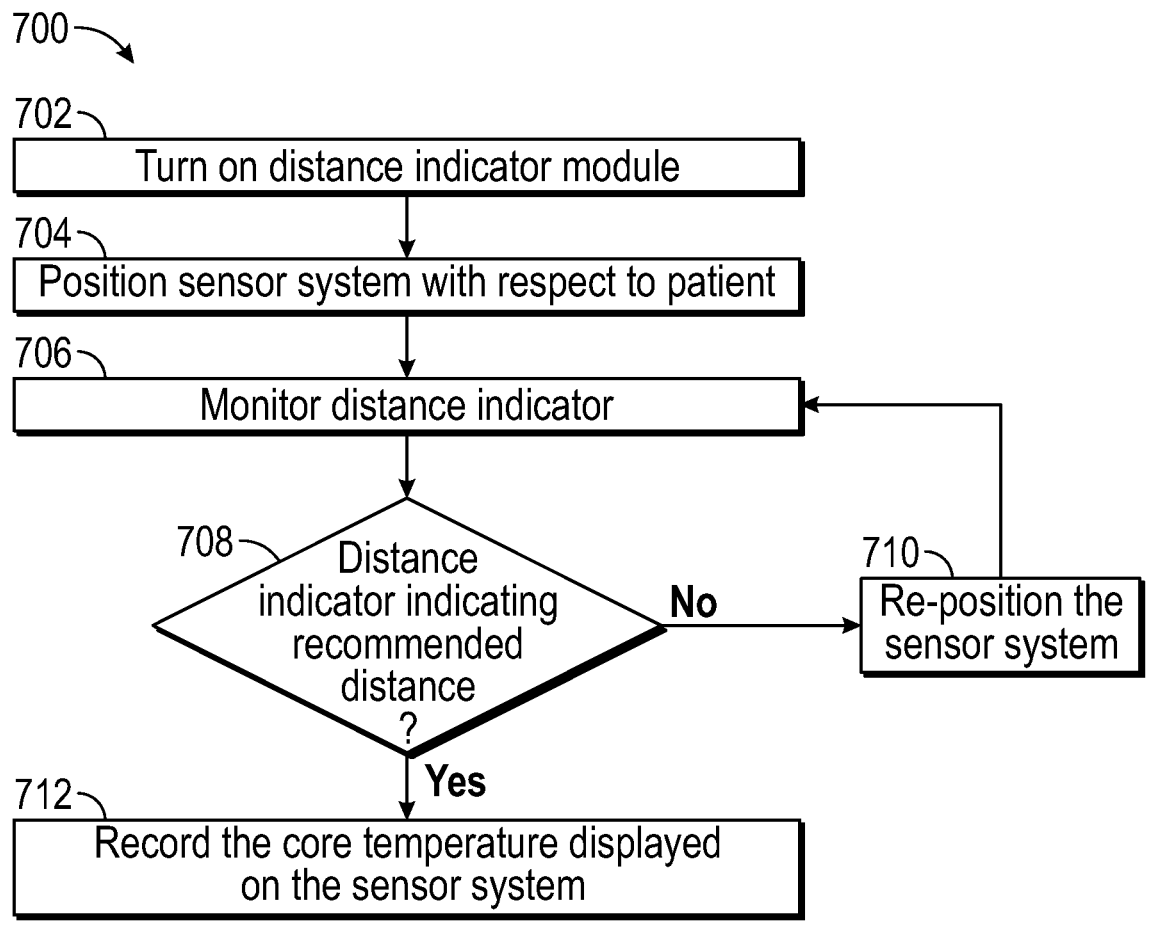
FIG. 7 illustrates an example method of orienting a sensor system with respect to a patient.
Figure 8A:
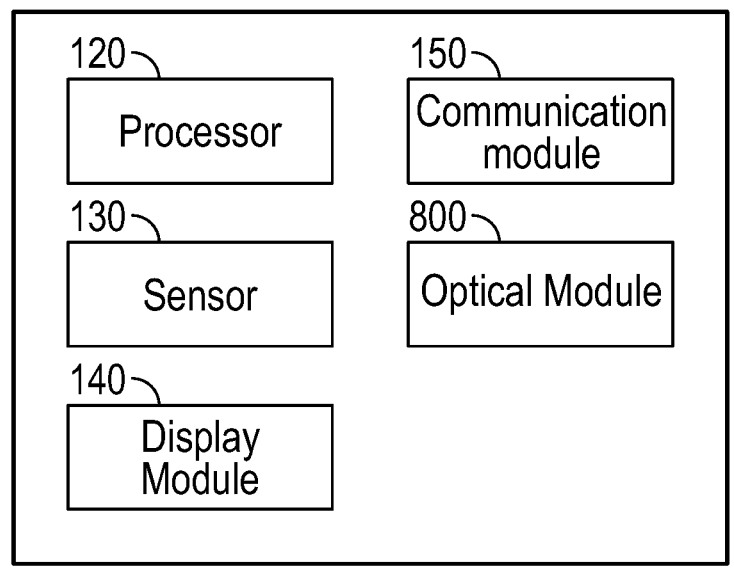
FIG. 8A is a block diagram illustrating of an example sensor system including an optical module.

FIG. 7 illustrates an example method 700 for correctly positioning the temperature measurement system 110 with respect to the patient. The temperature measurement system 110 may include a distance indicator module that may determine the distance between the temperature measurement system 110 and an object, for example, a patient. For example, the distance indicator module may be an optical module 800 as illustrated in FIG. 8A and described herein. In some examples, the distance indicator module can be the display module 140. At block 702, the processor 120 actuates the distance indicator module. At block 704, the temperature measurement system 110 is positioned with respect to the patient. At block 706, a distance indicator is monitored. In some examples, the distance indicator is generated by the display module 140. The distance indicator may be displayed on the temperature measurement system 110 or on the patient. The distance indicator may indicate whether the temperature measurement system 110 is positioned at a recommended distance from the patient.

In a non-limiting example, the distance indicator can include a first light beam in a first color and a second light beam in a second color. The first light beam and the second light beam may be generated by the same light source or different light sources. For example, the first color can be blue and the second color can be yellow. The first light source and the second light source can be oriented such that the first beam of light and the second beam of light can intersect at a predetermined distance.

At block 708, the processor 120 may determine whether the distance indicator indicates that the temperature measurement system 110 is at the recommended distance from the patient. The process of determining whether the distance indicator indicates that the temperature measurement system 110 is at the recommended distance from the patient may include determining the distance between the temperature measurement system 110 and an object, for example, a patient, and comparing the determined distance with a threshold distance value. When the temperature measurement system 110 is too close to the patient (including, for example, the distance between the temperature measurement system 110 and the patient is less than the recommended distance), the first beam and the second beam may be projected onto the patient at two different locations. Likewise, when the temperature measurement system 110 is too far from the patient (including, for example, the distance between the temperature measurement system 110 and the patient is greater than the recommended distance), the first beam and the second beam may be projected onto the patient at two different locations. However, when the temperature measurement system 110 is at the recommended distance from the patient, the two beams may be projected on the patient at the same location, displaying a third color different from the first color and the second color. For example, the third color can be green, which is a mix of blue and yellow. In this regard, care providers will be able to easily reorient the temperature measurement system 110 by monitoring where the two beams are on the patient.

In another example, the distance indicator projected on the patient may be visible or legible when the temperature measurement system 110 is positioned at a predetermined distance from the patient. The distance indicator, in some examples, may not be visible or legible when the temperature measurement system 110 is not positioned at the predetermined distance from the patient (including, for example, too close or too far from the patient). The distance indicator may be a temperature reading of the patient. According to one example, the distance indicator may be blurry when the temperature measurement system 110 is not positioned at a predetermined distance from the patient 100 and not blurry (including, for example, clearly legible or visible) when the temperature measurement system 110 is positioned at the predetermined distance from the patient 100. According to another example, the distance indicator may be out of focus when the temperature measurement system 110 is not positioned at a predetermined distance from a patient and in focus when the temperature measurement system 110 is positioned at the predetermined distance from the patient.

If the temperature measurement system 110 is not at the recommended distance, the temperature measurement system 110 can be re-positioned at block 710. In some examples, the temperature measurement 110 may generate and display a message, for example, via the display module 140, prompting a user to re-position the temperature measurement system 110. After the temperature measurement system 110 is re-positioned, the distance indicator can be monitored again to determine whether the temperature measurement system 110 is positioned at the recommended distance from the patient. If the temperature measurement system 110 is at the recommended distance, the estimated core body temperature displayed by the temperature measurement system 110 can be recorded at block 712.

FIG. 8A is a block diagram illustrating an example temperature measurement system 110 including an optical module 800. As noted above, the temperature measurement system 110, in addition to the optical module 800, can include the processor 120, the sensor 130, the display module 140, and the communication module 150. The processor 120 can communicate with the optical module 800 to calculate the distance between the temperature measurement system 110 and the patient 100.

Figure 8B:
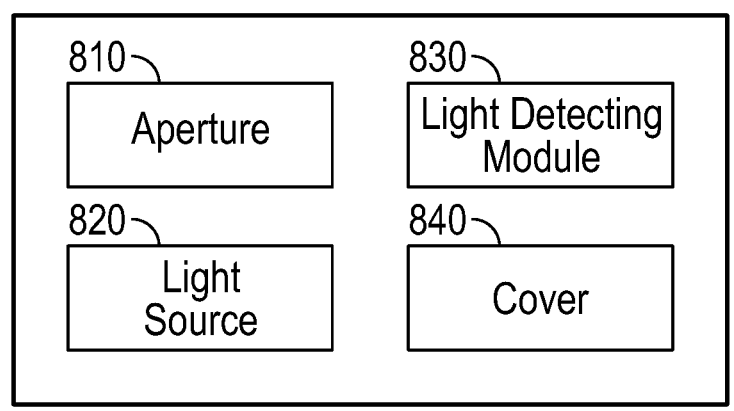
FIG. 8B is a block diagram illustrating the example optical module of FIG. 9A.

FIG. 8B is a block diagram illustrating the optical module 800. The optical module 800 can include an aperture 810, a light source 820, a light detecting module 830, and a cover 840. The aperture 810 can provide a path for infrared radiation to travel between the patient 100 and the temperature measurement system 110. In some implementations, the aperture 810 can provide a path for the light to travel from the light source 820 to another location, for example, skin of the patient. The light source 820 and the sensor 130 can be housed within the aperture 810. The aperture 810 can have a cross-sectional shape that is substantially parabolic. Such cross-sectional shape can aid in focusing an incoming light to the light detecting module 830. An inner surface of the aperture 810 can be reflective.

The light source 820 and the light detecting module 830 can be used to calculate the distance between the temperature measurement system 110 and the patient 100. The light emitted by the light source 820 can be reflected by the patient 100. The light detecting module 830 can detect the light reflected by the patient 100. The light detecting module 830 can detect one or more characteristics of the reflected light to determine the distance between the patient 100 and the temperature measurement module system 110. In some implementations, the light source 820 is a light emitter that generates infrared light.

The light detecting module 830 can detect the intensity of the reflected light. The intensity of the reflected light can inversely correspond to the distance between the patient 100 and the temperature measurement system 110. By determining the intensity of the reflected light (that is, reflected from the patient), the distance between the patient 100 and the temperature measurement system 110 can be calculated.

Additionally or alternatively, the light detecting module 830 can be a position-sensible photo detector that can determine light incident position of the reflected light. In some implementations, the conductivity of the light detecting module 830 can vary based on the incident position of the reflected light (for example, light reflected from or by the patient 100). In this regard, the conductivity of the light detecting module 830 can be used to calculate the distance between the patient 100 and the temperature measuring system 110.

The cover 840 can be coupled to the aperture 810. The cover 840 can be a closure mechanism for the aperture 810. The cover 840 can be a flap, a lid, a sliding panel, and the like. The cover 840 can include an open configuration and a closed configuration. When in the open configuration, the cover 840 can allow light emitted by the light source 820 (or light emitter) to travel between the temperature measurement system 110 to the patient 100. Moreover, the cover 840 in the open configuration can allow light to travel between the temperature measurement system 110 and the patient 100 such that the detecting module 830 can detect light reflected from the patient 100. When in the closed configuration, the cover 840 can prevent light from travelling between the temperature measurement system 110 and the patient 100.

In some examples, the cover 840 may be a lever arm that can be used to determine the distance between the temperature measurement system 110 and the patient. When actuated (for example, in an open configuration), the cover 840 can extend from the temperature measurement system 110 towards the patient. The length of the cover 840 may be substantially similar to the recommended distance between the sensor 130 and the patient as described herein. In some examples, the cover 840 may be extendable. When the cover 840 is not actuated (for example, in a closed configuration), it may cover the aperture 810.

The cover 840 can be actuated by an actuator, which may be actuated by a button, a switch, or a control knob, for example, on the temperature measurement system 110. Examples of actuators to open and close the cover 840 are mechanical actuators (such as a jack screw, spring, cam, wheel and axle, and the like), hydraulic actuators, magnetic actuators, piezoelectric actuators, twisted and coiled polymer (TCP) or supercoiled (SCP) actuators, thermal actuators, pneumatic actuators, and electro-mechanical actuators that can include a motor to actuate a mechanical actuator.

In some implementations, the cover 840 can be actuated automatically. For example, the actuator for the cover 840 can be actuated when the light source 820 is powered on (that is, generate a beam of light). In this regard, the cover 840 opens automatically when the user powers on the light source 820 to emit a beam of light towards the patient 100. Optionally, the cover 840 can be actuated automatically when the sensor 130 is powered on to detect infrared radiation from the patient 100.

The cover 840 can provide a waterproof or a water resistant barrier for the aperture 810, which can be advantageous in wet environments. Such feature can be especially helpful in hospital settings. In some implementations, the cover 840 can be manually actuated or removed. The cover 840 can be modular or integrated to the temperature measurement system 110.

Figure 9:
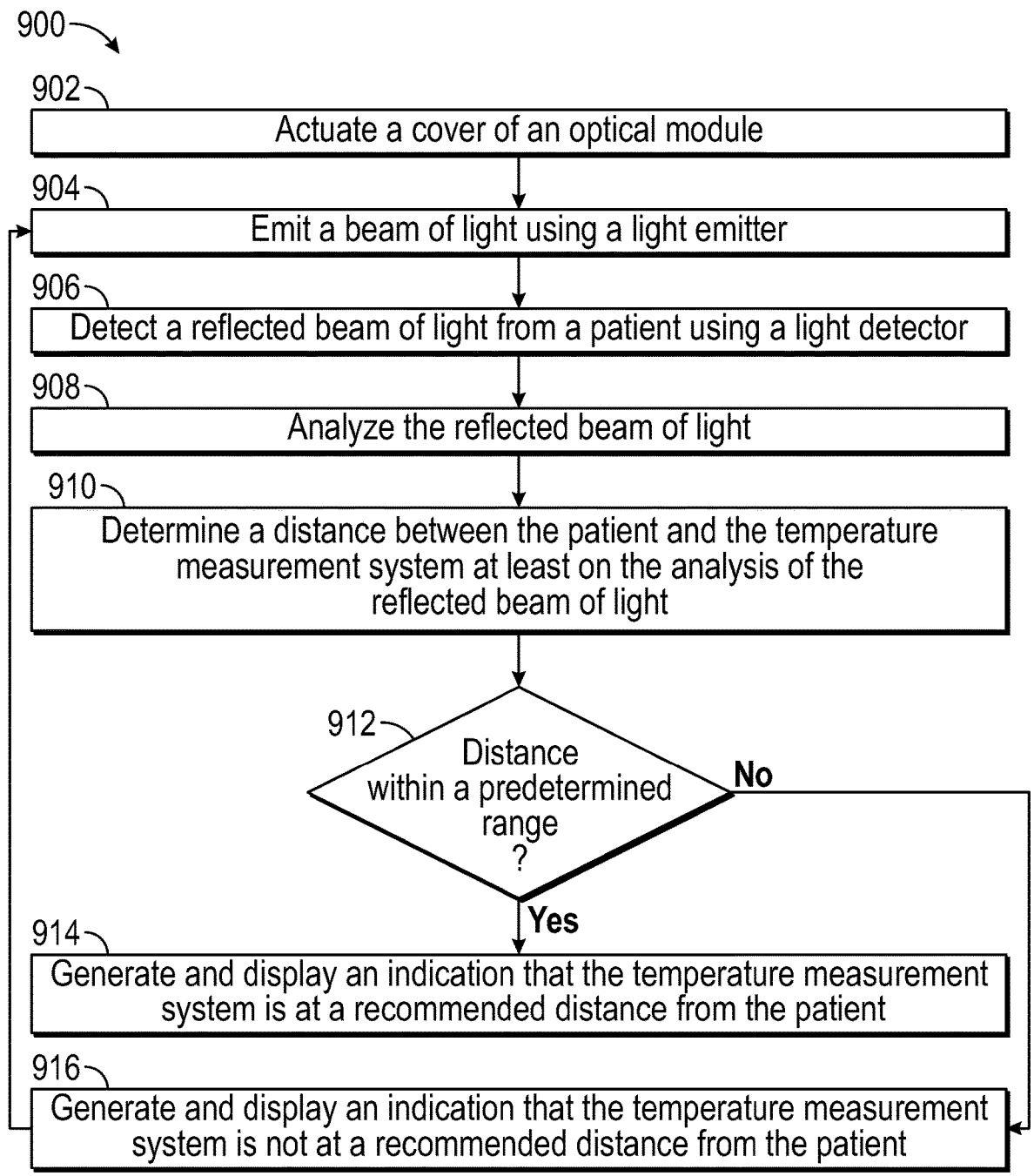
FIG. 9 illustrates an example method of generating and displaying an indication that the temperature measurement system is at a recommended distance from a patient.

FIG. 9 illustrates an example method 900 of generating and displaying an indicator that the temperature measurement system 110 is at a recommended distance from the patient 100. At block 902, the cover 840 is actuated. Actuating the cover 840 can change a configuration of the cover 840 from the closed configuration to the open configuration. When the cover 840 is in an open configuration, the light source 820 and the light detecting module 830 can be exposed such that light can travel between either of the light source 820 or the light detecting module 830 and the patient 100. At block 904, a beam of light can be emitted towards the patient 100 using the light source 820. The beam of light, once it reaches the patient 100, can be reflected by the patient 100 towards the temperature measurement system 110. At block 906, the reflected light can be detected using the light detecting module 830. At block 908, the detected reflected light is analyzed. As discussed herein, the detected reflected light can be analyzed to determine one or more characteristics. In some implementations, the light detector module 830 can determine an incident position of the reflected light. Optionally, the light detector module 830 can determine intensity of the reflected light.

At block 910, a distance between the temperature measurement system 110 and the patient 100 is determined. The distance can be calculated using the incident position of the reflected light or the intensity of the reflected light. At block 912, the distance between the temperature measurement system 110 and the patient 100 is compared to a predetermined range. The predetermined range can be indicative of recommended distance between the temperature measurement system 110 and the patient 100. The predetermined range can be varied for different sensors, different conditions, or different applications. For example, the predetermined range can be different when estimating core body temperature at different areas of the patient 100. In some implementations, the distance between the temperature measurement system 110 and the patient 100 is compared to a predetermined value (instead of a range).

At block 914, when the distance between the temperature measurement system 110 and the patient 100 is within the predetermined range, the temperature measurement system 110 can generate, for example, using a display module 140, a display indicating that the temperature measurement system 110 is at a recommended distance from the patient 100. On the other hand, when the distance between the temperature measurement system 110 and the patient 100 is not within the predetermined range, the temperature measurement system 110, at block 916, can generate a display indicating that the temperature measurement system 110 is not at a recommended distance from the patient 100. The method can return to the block 904 to emit another beam of light towards the patient 100.

Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain examples, acts or events can be performed concurrently, e.g., through multi-threaded processing, interrupt processing, or multiple processors or processor cores or on other parallel architectures, rather than sequentially. In addition, different tasks or processes can be performed by different machines or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry that can process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or methods illustrated can be made without departing from the spirit of the disclosure. As will be recognized, certain embodiments described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

What is claimed is:

1. A temperature measurement system for non-contact estimation of a core body temperature of a patient, the system comprising:
    a first temperature sensor comprising an infrared sensor, the first temperature sensor configured to detect infrared radiation from a skin surface of a patient when the first temperature sensor is distanced from the patient;
    a second temperature sensor different than the first temperature sensor, the second temperature sensor configured to detect an ambient air temperature of an area surrounding the patient; and
    a hardware processor programmed to execute software instructions to:
        access a first set of data from the first temperature sensor, the first set of data based on infrared radiation from the skin surface of the patient detected by the first temperature sensor, the first set of data representative of a surface temperature of the patient;
        calculate a mean surface temperature of the patient from the first set of data, the first set of data comprising a data subset;
        exclude a portion of the first set of data from the data subset within the first set of data based on differences between the mean surface temperature and data values of the portion of the first set of data exceeding a threshold, the threshold being based on a standard deviation of a distribution of differences between the mean surface temperature and data values of the first set of data;
        calculate another mean surface temperature of the patient from the data subset within the first set of data without the excluded portion of the first set of data;
        access a second set of data from the second temperature sensor, the second set of data representative of the ambient air temperature of the area surrounding the patient; and
        determine a core body temperature of the patient based at least in part on the another mean surface temperature and the second set of data.

2. The system of claim 1, wherein the hardware processor is programmed to execute the software instructions to discard a data point of the first set of data when a signal quality index (SQI) of the data point is less than an SQI threshold.

3. The system of claim 2, wherein the signal quality index is determined based at least in part on a standard deviation of the first set of data and a sensor tolerance associated with the first temperature sensor.

4. The system of claim 1, wherein the hardware processor is programmed to execute the software instructions to:
determine convective heat transfer between the skin of the patient and ambient air based at least in part on the first set of data and the second set of data; and
determine radiative heat transfer between the skin of the patient and the ambient air based at least in part on the first set of data and the second set of data,
wherein the core body temperature of the patient is determined based at least in part on the convective heat transfer and the radiative heat transfer.

5. The system of claim 1 further comprising:
a display module configured to generate an indicator for display, the indicator being associated with the core body temperature, the indicator having a first variable characteristic based at least on the core body temperature.

6. The system of claim 5, wherein the first variable characteristic is color of the indicator.

7. The system of claim 6, wherein the indicator has a first color when a predetermined condition is met, and wherein the indicator has a second color when the predetermined condition is not met.

8. The system of claim 5, wherein the indicator has a second variable characteristic based at least on the core body temperature, and wherein the second variable characteristic is a frequency at which the indicator blinks.

9. The system of claim 8, wherein the indicator blinks at a first frequency when the core body temperature satisfies a predetermined condition, and wherein the indicator blinks at a second frequency when the core body temperature does not satisfy the predetermined condition.

10. The system of claim 1, wherein the first temperature sensor comprises an infrared thermometer.

11. The system of claim 5, wherein the indicator is projected on the patient.

12. The system of claim 11, wherein the indicator is projected on an area of the patient from where the first set of data is taken.

13. The system of claim 5, wherein the indicator is legible when the first temperature sensor is positioned at a predetermined distance from the patient, and wherein the indicator is illegible when the first temperature sensor is not positioned at the predetermined distance from the patient.

14. The system of claim 1 further comprising:
a light source configured to emit a first beam of light towards the patient; and
a light detector configured to detect a second beam of light from the patient, wherein the second beam of light is a portion of the first beam of light reflected by the patient, and wherein the hardware processor is programmed to execute the software instructions to determine a distance between the first temperature sensor and the patient based on at least an intensity of the second beam of light or an incident position of the second beam of light within the light detector.

15. A method for determining a core body temperature of a patient, the method comprising:
accessing a first set of data from a first temperature sensor comprising an infrared sensor, the first set of data based on infrared radiation from a skin surface of the patient detected by the first temperature sensor when the first temperature sensor is distanced from the patient, the first set of data representative of a surface temperature of the patient;
calculating a mean surface temperature of the patient from the first set of data, the first of data comprising a data subset;
excluding a portion of the first set of data from the data subset within the first set of data based on differences between the mean surface temperature and data values of the portion of the first set of data exceeding a threshold, the threshold being based on a standard deviation of a distribution of differences between the mean surface temperature and data values of the first set of data;
calculating another mean surface temperature of the patient from the data subset within the first set of data without the excluded portion of the first set of data;
accessing a second set of data from a second temperature sensor different than the first temperature sensor, the second set of data representative of an ambient air temperature of an area surrounding the patient; and
determining a core body temperature of the patient based at least in part on the another mean surface temperature and the second set of data.

16. The method of claim 15 further comprising:
determining convective heat transfer between the skin of the patient and ambient air based at least in part on the first set of data and the second set of data; and
determining radiative heat transfer between the skin of the patient and the ambient air based at least in part on the first set of data and the second set of data,
wherein the core body temperature of the patient is determined based at least in part on the convective heat transfer and the radiative heat transfer.

17. The method of claim 15, further comprising discarding a data point of the first set of data when a signal quality index (SQI) of the data point is less than an SQI threshold.

18. The method of claim 17, further comprising determining the signal quality index based on at least a standard deviation of the first set of data and a sensor tolerance associated with the first temperature sensor.

19. The method of claim 15 further comprising:
generating an indicator for display, the indicator being associated with the core body temperature, the indicator having a first variable characteristic based at least on the core body temperature.

20. The method of claim 15 further comprising:
emitting a first beam of light towards the patient;
detecting a second beam of light from the patient, wherein the second beam of light comprises a portion of the first beam of light reflected by the patient; and
determining a distance between the first temperature sensor and the patient based on at least an intensity of the second beam of light or an incident position of the second beam of light within a light detector.

* * * * *